(12) United States Patent
Chuard et al.

(10) Patent No.: US 6,680,003 B2
(45) Date of Patent: Jan. 20, 2004

(54) CHIRAL DOPING AGENTS WITH VARIABLE SPIRAL PITCH INDUCTION AND APPLICATION THEREOF TO A REFLECTIVE COLOR DISPLAY

(75) Inventors: Thierry Chuard, Les Geneveys-sur-Coffrane (CH); Robert Deschenaux, La Chaux-de-Fonds (CH); Rolf Klappert, Neuchâtel (CH); Séverine Meyer, Neuchâtel (CH)

(73) Assignee: Asulab S.A., Marin (CH)

( * ) Notice: Subject to any disclaimer, the term of this patent is extended or adjusted under 35 U.S.C. 154(b) by 199 days.

(21) Appl. No.: 10/000,331

(22) Filed: Dec. 4, 2001

(65) Prior Publication Data

US 2002/0114902 A1 Aug. 22, 2002

(30) Foreign Application Priority Data

Dec. 18, 2000 (EP) .............................. 00204584

(51) Int. Cl.[7] .............................. C09K 19/58
(52) U.S. Cl. ................ 252/299.2; 428/1.1; 252/299.01
(58) Field of Search .................... 252/299.01, 299.1, 252/299.2, 299.3, 299.4, 299.5, 299.6, 299.61, 299.62, 299.63, 299.64, 299.65, 299.66, 299.67, 299.68, 299.7; 428/1.1, 1.4

(56) References Cited

FOREIGN PATENT DOCUMENTS

| DE | 195 20 704 | 12/1996 |
| DE | 197 38 642 | 3/1999 |
| DE | 198 59 584 | 6/2000 |
| EP | 0 755 915 | 1/1997 |
| WO | 98 34 995 | 8/1998 |
| WO | 98 55 473 | 12/1998 |

OTHER PUBLICATIONS

Witte Van De P et al: "Modification of the Pith of Chiral Nematic Liquid Crystals by Means of Photoisomerization of Chiral Dopants" Liquid Crystals, GB, Taylor and Francis, Ltd., London, vol. 24, No. 6, Jun. 1, 1998, pp. 819–827.

Yarmolenko S N et al : "Photosensitive Chiral Dopants with High Twisting Power", Liquid Crystals, GB, Taylor and Francis, LTd., London, vol. 16, No. 5, May 1, 1994, pp. 877–882.

*Primary Examiner*—Mark F. Huff
*Assistant Examiner*—Jennifer R. Sadula
(74) *Attorney, Agent, or Firm*—Sughrue Mion, PLLC

(57) ABSTRACT

The present invention concerns chiral doping agents allowing a modification to be induced in the spiral pitch of a cholesteric liquid crystal, said doping agents including a biactivated chiral unit at least one of whose functions allows a chemical link to be established with an isomerisable group, for example by radiation, said group possibly having a polymerisable or co-polymerisable end chain. These new chiral doping agents find application in particular in a color display.

16 Claims, 5 Drawing Sheets

CHIRAL DOPING AGENTS WITH VARIABLE SPIRAL PITCH INDUCTION AND APPLICATION THEREOF TO A REFLECTIVE COLOR DISPLAY

The present invention concerns a new family of chiral doping agents with variable spiral pitch induction, i.e. chemical compounds which, when added in small quantities to a nematic type liquid crystal composition, allow a variable spiral pitch to be induced as a function of isomerisation of part of the chemical structure, for example by means of appropriate irradiation whose wavelength may vary from the ultraviolet (UV) to the visible (VIS), or by means of a heat gradient.

The invention concerns more particularly such chiral doping agents in which the end chains include a polymerisable moiety allowing the spiral pitch induced by isomerisation to be fixed, and thus one or more determined colours to be fixed by using a single liquid crystal composition to which is added a single chiral doping agent according to the invention or a single composition of said chiral doping agents.

In displays operating in reflective mode using chiral nematic phase materials, also designated by the term "cholesteric", fixing a colour is known by using:

a purely optical active substance having a chiral nematic phase, a mixture of optically active substances, all having a chiral nematic phase, or a substance or a mixture of chiral substances having a nematic phase and containing one or more optically active substances, i.e. chiral doping agents able to be mesomorphic or not and capable of inducing helicity having a determined pitch in the whole mesophase to form a cholesteric phase.

The compounds according to the present invention correspond to the chiral doping agents of the last category and belong more generally to the category of photochemical molecular switches, certain families of which have already been the subject of numerous studies and publications which are cited hereinafter by way of non-exhaustive illustration.

Photoracemisation of binaphtyl and its derivatives, and their helicity induction capacity in the nematic medium have been the subject of in-depth studies in particular by H. J. Deussen & al (Liq. Cryst. 1996, 21, 327; Mat. Res. Soc. Symp. Proc. 1996, 425, 55). It appears however that the photoisomerisation of these compounds involves significant decomposition which is detrimental to the persistence of a determined colour.

B. L. Feringa & al (J. Am. Chem. Soc. 1991, 113, 5468) studied thioxanthene type compounds which isomerise reversibly between two diastereoisomeric forms, with the object of applying this system to the reversible storage of information and thus also allowing application to a colour display. These compounds have the drawback however of having insufficient chemical stability and a switching speed which is much too long (several minutes, or even hours), incompatible for example with a digital display in a timepiece. In the same field, B. L. Feringa's team also studied derivatives of the dithienylethene type photoisomerisable between an open shape and a closed form (L. N. Lucas & al Chem. Commun. 1998, 2313; Tetrahedron Lett. 1999, 40, 1775).

G. B. Schuster & al (J. Am. Chem. Soc. 1995, 117, 8524) made use of the work of Y. Yokoyama & al (J. Am. Chem. Coc., Com. 1995, 785) on fulgide derivatives to modify the helicity of a cholesteric material. It appears however that a high concentration ($\geq 5\%$) of fulgide derivatives is required to obtain only a moderate change in the spiral pitch (approximately 30%).

H. Hattor & al (Liq. Cryst. 1999, 26, 1085; J. Polym. Sci. 2000, 38, 887) studied spiropyrane derivatives, and more particularly compounds obtained via the co-polymerisation of a cholesterol derivative with different monomers containing a spiropyrane unit activated on positions other than the nitrogen. It appears however that the modification of HTP by UV exposure is insufficient and that modification of the colour reflected by this material ($\Delta \lambda$ approximately 10 nm) is insufficient to cover the visible spectrum and envisage making a trichromatic display.

The works of S. N. Yarmolenko & al (Liq. Cryst. 1994, 16, 877) on photomodulable chiral units derived from menthyl and the works of R. P. Lemieux & al (Liq. Cryst. 1996, 20, 741; J. Am. Chem. Soc. 1997, 119, 8111) on photomodulable chiral units derived from thioindigo may also be cited.

The chiral molecular photo-switches, whose features were briefly recalled hereinbefore, practically all integrate the chiral unit and the photoactive unit in a single entity.

The chiral doping agents according to the present invention however include a two-functional chiral unit, at least one of whose functions allows a chemical bond to be established between an isomerisable group and thus allows a separate isomerisable group from the chiral unit to be obtained. In a preferred embodiment, the isomerisable group has a polymerisable or co-polymerisable end chain.

Thus the chiral doping agents according to the invention have three essential structural characteristics by UV or VIS radiation and/or by the addition of photoinitiators:

a biactivated central chiral unit allowing helicity induction in the nematic phase, at least an isomerisable unit allowing the molecular structure to be varied and thus the helicity to be modulated in the nematic phase, and polymerisable functions allowing, on the one hand the molecules to be in a way attached by each end and the isomerisation reaction to be blocked at a determined spiral pitch, thus at a determined colour, and on the other hand, via the formation of a gel, preventing the phenomena of diffusion from one pixel to another when one wishes to realise a trichromatic display, as will be explained in the detailed description.

In the following description, "the isomerisable unit" will be named "photoisomerisable unit" assuming that isomerisation is obtained by UV or VIS radiation, the chiral doping agents according to the invention then being named photomodulable chiral doping agents.

Other features and advantages of the present invention will appear more clearly upon reading the following detailed description, with reference to the annexed drawings, in which.

Figure 1:
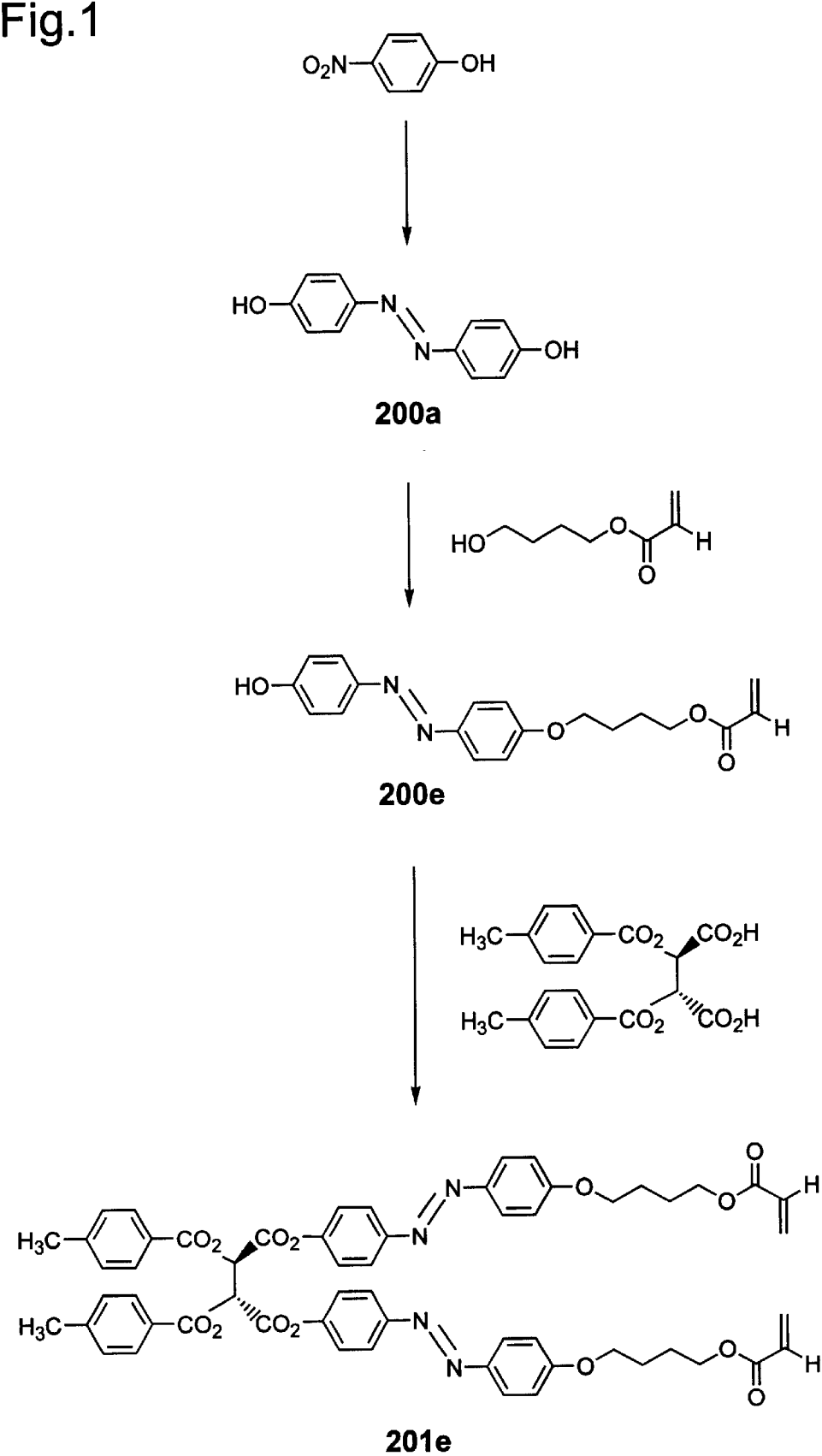
FIG. 1 shows a synthesis diagram of a chiral doping agent according to the invention.

The photomodulable chiral doping agents according to the present invention answer more precisely the following formula I:

$$A_1—Y_1—X—Y_2—A_2 \qquad (I)$$

wherein
X represents a chiral radical derived from a biactivated compound, such as diacids or diols,
$Y_1$ and $Y_2$ are identical or different and each represents a functional link unit selected from among —O—, —S—, —COO—, —OCO—, CON(R)—, —N(R)CO—where R represents an alkyl moiety,
$A_1$ represents a photomerisable group corresponding to the formula (II)

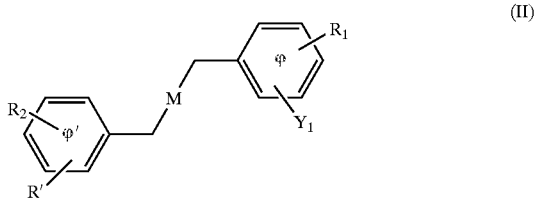
(II)

wherein two phenyl moieties φ and φ' are linked by a photomerisable bivalent radical —M— selected from among —N=N—, —N=CH—, —CH=N— and —CH=CH—; said phenyl moieties respectively having one or more identical or different substituents $R_1$, $R_2$ selected from among hydrogen, the alkyl or alkoxy radicals from $C_1$ to $C_5$, halogens and the cyano, nitro or trifluoromethyl radicals; and R' represents hydrogen or a group corresponding to the formula (III)

$$-Y_3-C_nH_{2n}-Z \qquad (III)$$

wherein $Y_3$ has the same significance as $Y_1$ and $Y_2$ or represents phenylene, n may take the values from 0 to 12 and Z represents hydrogen or a polymerisable moiety selected from among the acryloyl and acryloylxy moieties; and
$A_2$ has the same significance as the groups of formula (II) or formula (III).

Among the chiral diacids and diols, leading to chiral radical X of formula (I), one may cite tartric di-O,O'-p-toluyl tartric acid di-O, O'-p-pivaloyl tartaric acid, 1,2 dicarboxylic cyclohexane acid, camphric acid, tartric isopropylidene acid, 3-methyladipidic acid, and dianhydro-glucitol and dianhydro-mannitol, these two diols allowing synthesis of the preferred compounds as will be seen hereinafter.

The photoisomerisable unit represented by $A_1$ and/or $A_2$ in formula (I) has azophenyl as its basic structure when M represents —N=N—, azomethine when M represents —N=CH— and stilbene when M represents —CH=CH—. As will be seen hereinafter, the basic structure corresponding to azophenyl has been retained by way of illustration since it is a simple, easily synthesised structure whose trans⇌cis equilibrium is well known, with a displacement towards the cis form by radiation at a wavelength λ of <400 nm, and a displacement towards the trans form thermally or by radiation at a wavelength λ of >400 nm.

A compound answering the general formula I, and whose characteristics and properties will be described hereinafter, is for example the compound referenced 209s answering the formula hereinafter

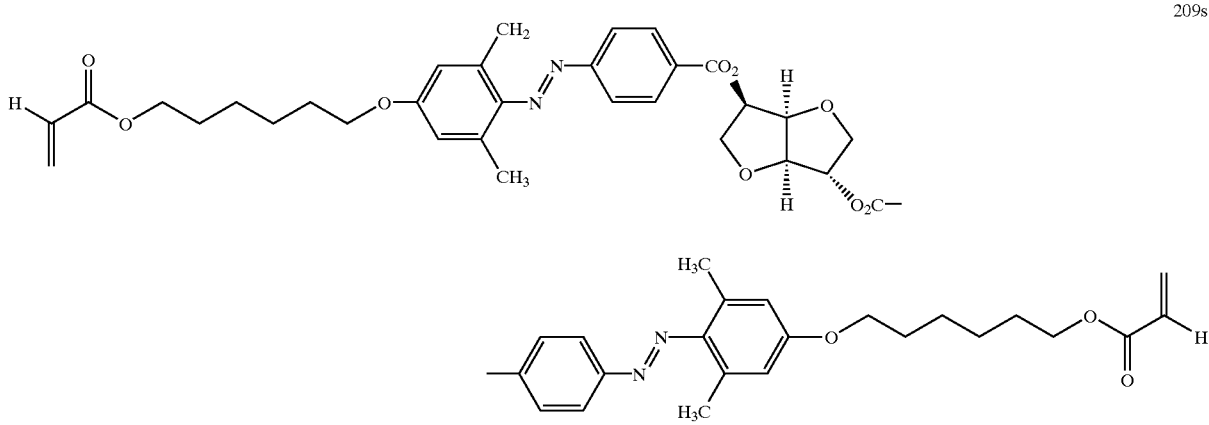
209s wherein the chiral radical X derives from 1,4;3,6-dianhydro-D-glucitol, $Y_1$ and $Y_2$ each representing —COO—, $A_1$ and $A_2$ are identical and each represent an azophenyl radical (—M—=—N=N—), of which a non-substituted ($R_1$=H) phenyl moiety (φ) is linked in para position to —COO—, and the other phenyl moiety (φ') of which disubstituted in 2',5' by a methyl radical ($R_2$=$CH_3$) further includes in para a chain including successively —O—(=$Y_3$), the hexamethylene radical (n=6) and a acryloyloxy polymerisable moiety (=Z).

The chemical structures of other compounds illustrating the family of chiral doping agents according to the invention will be reported in Table 1 hereinafter with their physico-chemical characterisation (melting/enthalpy point; elemental analysis).

TABLE 1

| Reference | Structure | F °C. (ΔH k/mol) | % | Calc. | Actual |
|---|---|---|---|---|---|
| 201b | 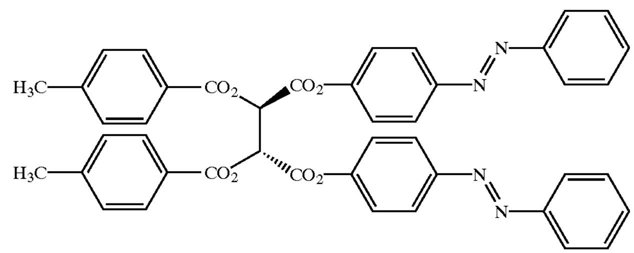 | 213 (69) | C<br>H<br>N | 70.77<br>4.59<br>7.50 | 70.73<br>4.67<br>7.57 |
| 201c | 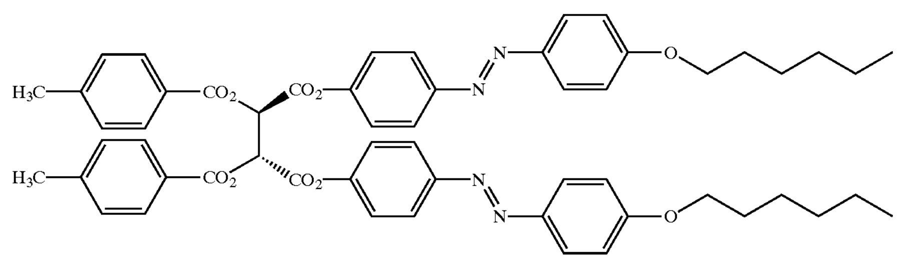 | 159 (67) | C<br>H<br>N | 71.02<br>6.17<br>5.92 | 70.82<br>6.15<br>5.84 |
| 201e | 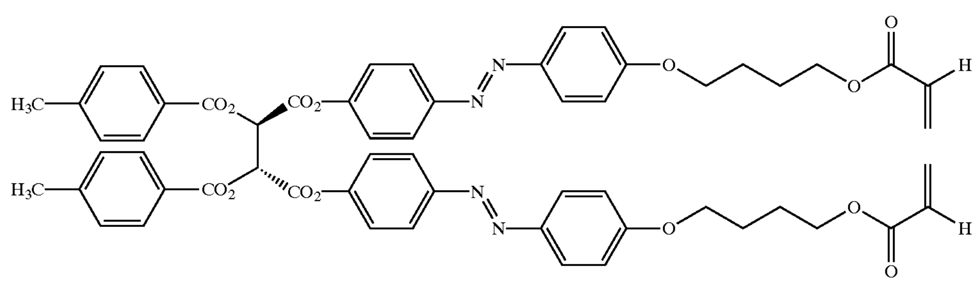 | 134 (40) | C<br>H<br>N | 67.56<br>5.28<br>5.43 | 67.50<br>5.27<br>5.41 |

TABLE 1-continued

| Reference | Structure | F° C. (ΔH k/mol) | Calc. | Actual |
|---|---|---|---|---|
| 202c | 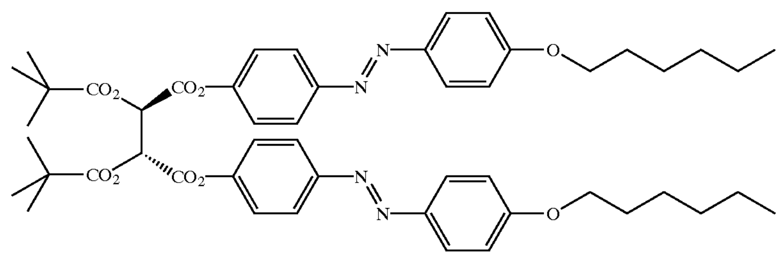 | 149 (44) | C 68.32<br>H 7.11<br>N 6.37 | 68.33<br>7.10<br>6.34 |
| 203b | 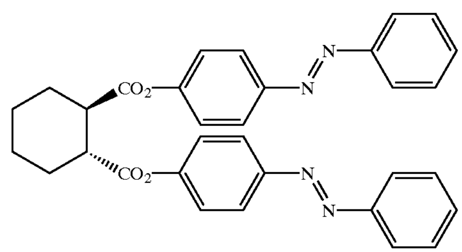 | 165 (58) | C 72.17<br>H 5.30<br>N 10.52 | 71.99<br>5.40<br>10.28 |
| 203c | 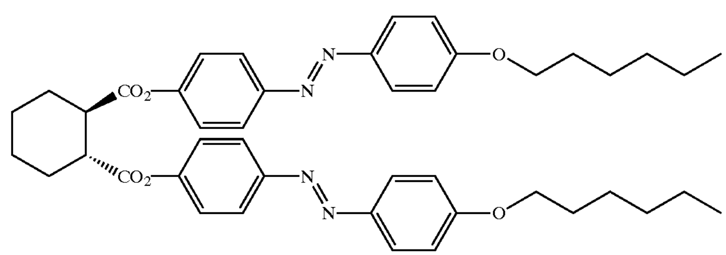 | 195 (64) | C 72.11<br>H 7.15<br>N 7.64 | 72.02<br>7.10<br>7.71 |

TABLE 1-continued

| Reference | Structure | F °C. (ΔH kj/mol) | | |
|---|---|---|---|---|
| | | | Calc. | Actual |
| 204c | (structure) | 150 (46) C H N | 72.61 7.42 7.36 | 72.56 7.40 7.31 |
| 206c | (structure) | 133 (57) C H N | 68.78 6.71 7.46 | 68.77 6.74 7.36 |

TABLE 1-continued

| Reference | Structure | F° C. (ΔH k/mol) | | |
|---|---|---|---|---|
| | | | Calc. | Actual |
| 306c | 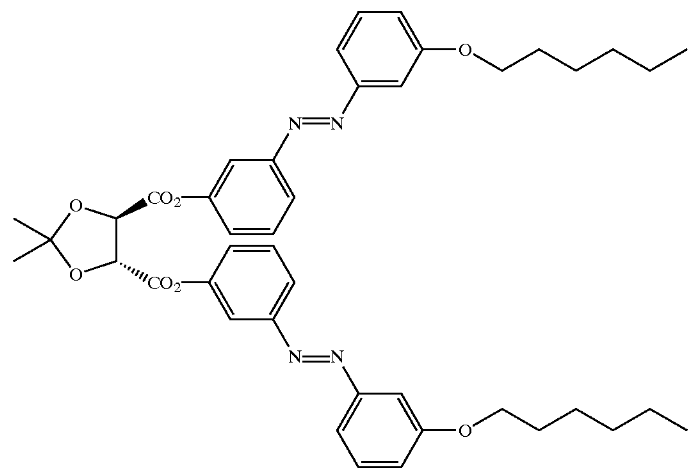 | 63 (41) | | |
| | | C | 68.78 | 68.82 |
| | | H | 6.71 | 6.82 |
| | | N | 7.46 | 7.20 |
| 206e | 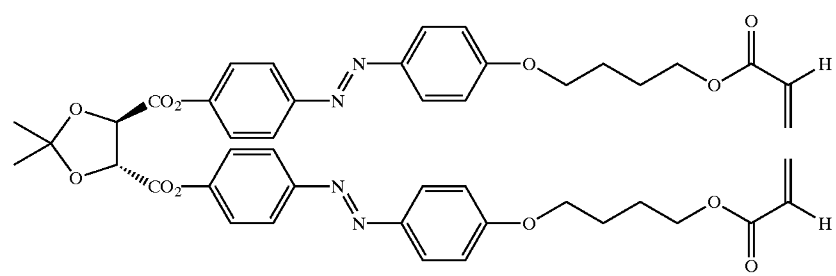 | 121 (41) | | |
| | | C | 64.67 | 64.58 |
| | | H | 5.55 | 5.69 |
| | | N | 6.71 | 6.65 |

TABLE 1-continued

| Reference | Structure | F ° C. (ΔH kJ/mol) | | |
|---|---|---|---|---|
| | | | Calc. | Actual |
| 207c | (structure) | 151 (35) C H N | 71.64 7.27 7.77 | 71.57 7.53 7.66 |
| 209g | (structure) | 204 (62) C H N | 69.27 6.61 7.34 | 69.22 6.87 7.47 |
| 209j | (structure) | 169 (58) C H N | 66.51 6.03 6.20 | 66.25 6.13 6.39 |

TABLE 1-continued

| Reference | Structure | F °C. (ΔH k/mol) | | |
|---|---|---|---|---|
| | | % | Calc. | Actual |
| 209s | 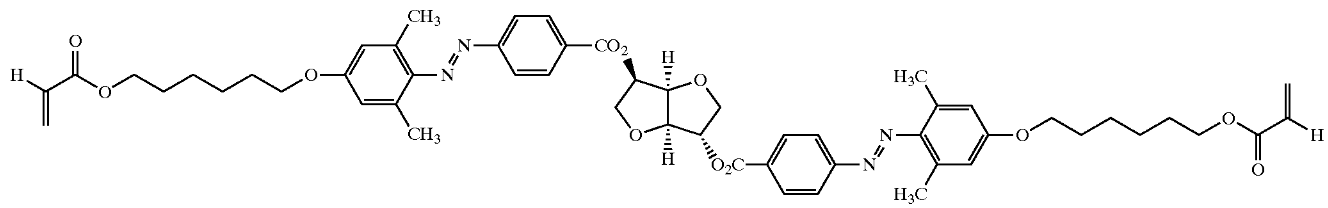 | 93 (66) C H N | 67.63 6.52 5.84 | 67.61 6.56 5.91 |
| 209sf | 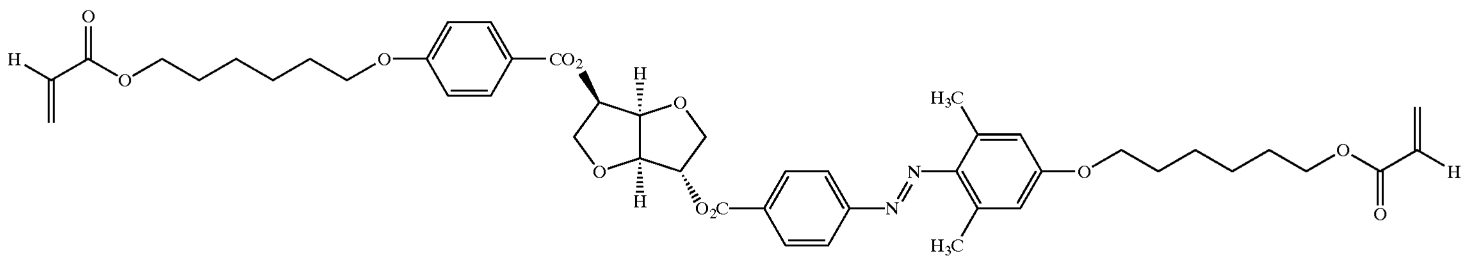 | 90 (44) C H N | 66.81 6.58 3.39 | 66.80 6.51 3.34 |
| 209fs | 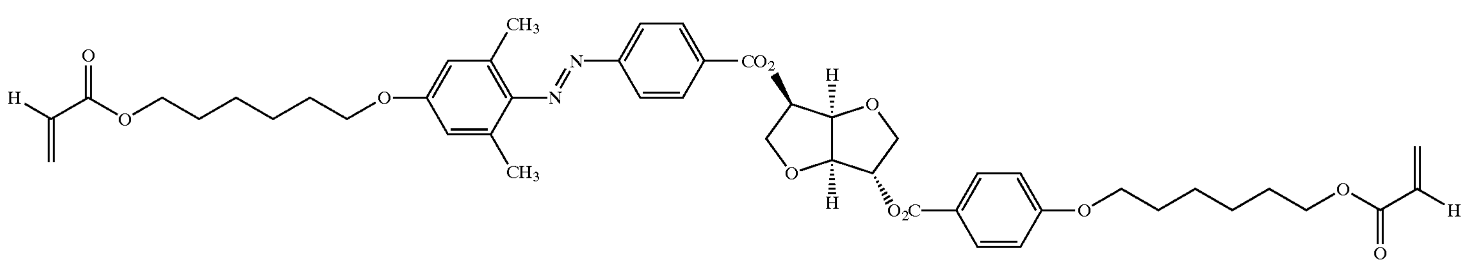 | 89 (46) C H N | 66.81 6.58 3.39 | 66.78 6.77 3.49 |

TABLE 1-continued

| Reference | Structure | F° C. (ΔH k/mol) | Calc. | Actual |
|---|---|---|---|---|
| 209sa | (structure) | 53 (45) | C 65.33<br>H 6.31<br>N 4.62 | 65.27<br>6.48<br>4.58 |
| 210fs | (structure) | 68 (48) | C 66.81<br>H 6.58<br>N 3.39 | 66.77<br>6.78<br>3.47 |

With reference now to the synthesis diagram shown in annexed FIG. 1, the synthesis of a photoisomerisable and polymerisable compound having the reference 201e in Table 1 will be described hereinafter.

EXAMPLE 1

Synthesis of 2,3-Bis[di-4, 4' (4-acryloyloxybutyloxy) azophenyl-carbonyloy]-di-O, O'-p-toluyl-L-tartrate (Ref 201 e)

Synthesis of this compound is effected in three steps.

1st Step: Preparation of the 4.4'-Hydroxy-azobenzene Intermediate (200a)

10.0 g (71.9 mmol) of 4-nitrophenol are finely pounded in a mortar with 50.0 g (891.0 mmol) of KOH. The mixture is placed in a porcelain cupel, 10 ml of water are added and the mixture is gently heated and stirred until a homogenous paste is obtained. The heat is then increased and the mixture progressively passes from yellow to violet-black in a vigorous reaction with gas emission. When the gas emission has finished, heating is then stopped. The solid is dissolved while still hot in a minimum of water (approx. 150 ml) and the pH of the solution thereby obtained is brought to between 8 and 9 while being stirred with HCl 5N. A colour change from dark brown to beige occurs in addition to the formation of a precipitate which is filtered on a Büchner funnel and vacuum oven dried in the presence of $P_2O_5$ to give 5.8 g of raw product. The latter is purified by silicon gel chromatography with ether as eluant. The fraction containing the pure product is evaporated to dryness, giving 4.62 g of product corresponding to the reference 200a (60% yield).

2nd Step: Preparation of the 4-Hydroxy-4'(4-acryloyloxybutyloxy)-azobenzene Intermediate (200e)

0.8 g (3.73 mmol) of compound 200a and 0.54 g (3.73 mmol) of 4-hydroxybutylacrylate are dissolved in 20 ml of dry THF. 1.00 g (3.8 mmol) of triphenylphosphine are added and the solution is cooled to 0° C. 1.7 ml (3.74 mmol) of a solution of 40% DEAD (diethylazodicarboxylate) in toluene are added drop by drop then left to react overnight at ambient temperature. The solvent is removed in a rotating evaporator to give 3.2 g of raw product which is purified by silicon gel chromatography with a $CH_2Cl_2$/AcOEt (97:3) eluant. After removing the solvent, one of the fractions collected allows 0.48 g of product to be obtained corresponding to the reference 200e (36% yield).

3rd Step: Obtaining the Title Compound 0.49 g (1.28 mmol) of (−)-di-O,O'-p-toluyl-L-tartric acid, 0.55 g (2.67 mmol) of DCC (N,N'-dicyclohexylcarbodiimide) and 0.8 g (2.68 mmol) of compound 200e are dissolved in 70 ml of dry $CH_2Cl_2$ and cooled to 0° C. 0.04 g (0.33 mmol) of 4-DMAP (4-dimethylamino pyridine) are added and the reactional mixture is stirred for seven hours at 0° C. before being washed with HCl 0.01 N. The organic phase is dried on $MgSO_4$ and the solvent removed in a rotating evaporator, to give 1.62 g of raw product. The latter is purified by silicon gel chromatography with, at the beginning, an eluant of $CH_2Cl_2$/AcOEt (98:2), then $CH_2Cl_2$/AcOEt (94:6). 0.76 g of product are isolated and hot recrystallised in EtOH, to give 0.40 g of the title product (33% yield).

In addition to the characteristics listed in Table 1, the nuclear magnetic resonance spectrum and mass spectrum were also effected which confirm the structure and purity of the expected product:

$^1$H-RMN (200 MHz, $CDCl_3$): 1.82–1.98 (m, 8H, aliph.); 2.45 (s, 6H, $CH_3$); 4.09 (t, 4H, $OCH_2$); 4.26 (t, 4H, $CO_2CH_2$); 5.82 (dd, 2H, vinyl.); 6.13 (dd, 2H, vinyl.); 6.40 (s, 2H, CH); 6.42 (dd, 2H, vinyl.); 6.99 (d, 4H, arom.); 7.19 (d, 4H, arom.); 7.31 (d, 4H, arom.); 7.85 (d, 4H, arom.); 7.88 (d, 4H, arom.); 8.10 (d, 4H, arom.). MS: 1031 $(M+H)^+$.

Figure 2:
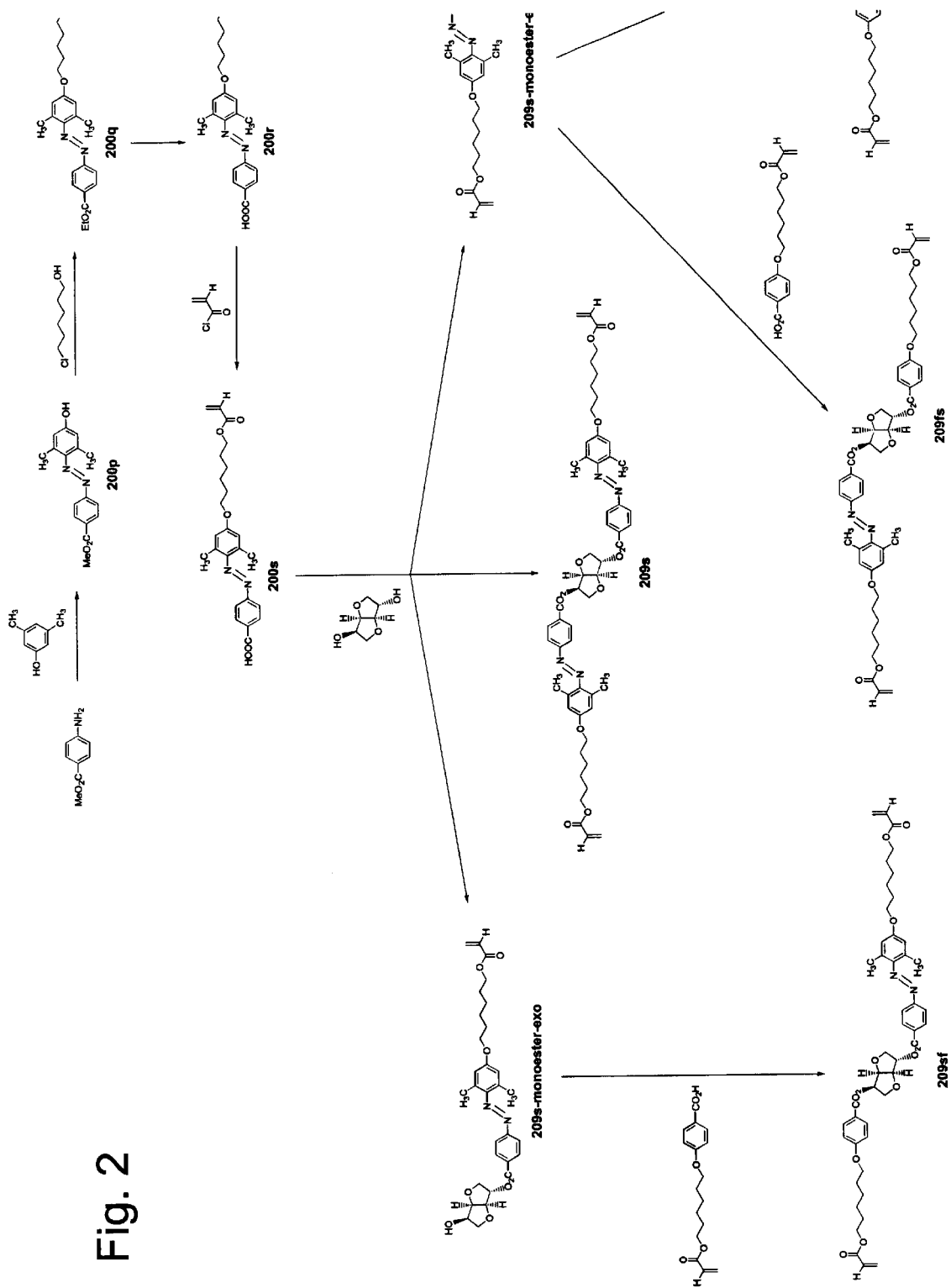
FIG. 2 shows a synthesis diagram of four chiral doping agents according to the invention from a common synthesis intermediate.

With reference now to the synthesis diagram shown in annexed FIG. 2, the synthesis of the compounds having the references 209s, 209sf, 209fs and 209sa in Table 1 will be described in examples 2 to 5 hereinafter.

EXAMPLE 2

Synthesis of 2.5 Bis[4'-(6-acryloyloxyhexyloxy)-2.5'-methylazophenyl-4-carbonyloyl]-1.4;3.6-dianhydro-D.glucitol (209s)

This synthesis is effected in five steps since it is necessary to prepare a reactive form of substituted azobenzene, which is not a commercial product.

1 st Step: Preparation of the 2.5-Dimethyl-4-hydroxy-4'-methoxycarbonyl-azobenzene Intermediate (200p)

5.00 g (33.1 mmol) of methyl 4-aminobenzoate are dissolved in 40 ml HCl 3N and cooled to 0° C. A solution of 2.76 g (40.0 mmol) of $NaNO_2$ in 15 ml of water is added drop by drop then the mixture is stirred for an other hour at 0° C. 0.57 g (9.54 mmol) of urea are added to destroy the excess $NaNO_2$. The reactional mixture is then poured into a solution at 0° C. of 4.04 g (33.1 mmol) of 3,5-dimethylphenol in 40 ml of NaOH 2N causing the formation of a very dense orange precipitate. The precipitate is filtered on a Büchner funnel and vacuum oven dried in the presence of $P_2O_5$, leading, after hot recrystallisation in toluene to 7.83 g of product having the reference 200p (83% yield).

2nd Step: Preparation of the 2.5-Dimethyl-4-(6-hydroxyhexyloxy) Azobenzene Intermediate (200g)

8.00 g (28.1 mmol) of 200p are dissolved in 160 ml of dry EtOH and 1.13 g (28.2 mmol) of NaOH are added. The mixture is refluxed with heating and 3.80 g (27.8 mmol) of 6-chloro-1-hexanol are added. The reflux is maintained for six days adding two further portions of 3.80 g (27.8 mmol) of 6-chloro-1-hexanol (after one and four days of reaction respectively). After cooling, the mixture is concentrated to approximately 100 ml in a rotating evaporator apparatus and decanted into a separating funnel. 300 ml of ether are added and the organic phase is washed with HCl 1N. As the aqueous phase is orange-coloured, the latter is extracted once with ether. The organic phases are grouped, dried over $MgSO_4$ and the solvent is removed in a rotating evaporator apparatus, giving a viscous residue which is purified by silicon chromatography with a $CH_2Cl_2$/AcOEt (95:5) eluant. This operation allows a fraction containing the product referenced 200q to be obtained, which is evaporated to dryness to give 11.7 g of product in oily form.

3rd Step: Preparation of the 2'.5'-Dimethyl-4'-(6-hydroxyhexyloxy)-4-azophenylcarboxylic Acid Intermediate (200r)

The oil obtained in the preceding step (11.7 g) is dissolved in 150 ml of EtOH and 200 ml of water containing 9.00 g (225 mmol) of NaOH are added and the mixture is refluxed with heating for three hours. After cooling, the mixture is poured into a water/ice bath and the solution is acidified with HCl 5N. The orange precipitate is filtered on a Büchner funnel and vacuum oven dried in the presence of $P_2O_5$. Hot recrystallisation in AcOEt gives 3.46 g of product having the reference 200r (33% yield calculated from the initial quantity of 200p).

4th Step: Preparation of the 2'.5'-Dimethyl-4'-(6-acryloyloxyhexyloxy)-4-azophenylcarboxylic Acid Intermediate (200s)

3.00 g (8.10 mmol) of 200r and 2.40 g (19.8 mmol) of N,N-dimethylaniline are dissolved, by heating if necessary in 200 ml of THF (tetrahydrofurane). 0.90 g (9.94 mmol) of acryloyle chloride are added at ambient temperature. The mixture is stirred for two days at ambient temperature adding a further 2.40 g (19.8 mmol) of N,N-dimethylaniline and 0.90 g (9.94 mmol) of acryloyle chloride after one day. The reactional mixture is decanted into a separating funnel, 200 ml of ether are added and the organic phase is washed with HCl 2N. The organic phase is dried and the solvent removed in a rotating evaporator. The residue is purified by silicon gel chromatography with ether as eluant. The fraction containing the pure product is evaporated to dryness, leading to 3.16 g of product having the reference 200s (92% yield) which can be recrystallised in an ether/hexane mixture.

Step 5: Obtaining the Title Product 2.23 g (5.33 mmol) of 200s are dissolved in 200 ml of DME (1.2-dimethoxyethane) and cooled to −25° C. 0.60 g. (5.24 mmol) of $CH_3SO_2Cl$ then 1.10 g (10.87 mmol) of TEA (triethylamine) are added and the mixture is kept one hour at −25° C. 0.36 g (2.46 mmol) of dianhydro-D-glucitol and 0.65 g (5.32 mmol) of 4-DMAP are added. Cooling is stopped and the reactional mixture is stirred for another three days at ambient temperature before being hydrolysed with diluted aqueous HCl and decanted into a separating funnel. 200 ml of $CH_2Cl_2$ are added then the organic phase is separated, dried on $MgSO_4$ and the solvent removed in a rotating evaporator. The residue is purified by two successive silicon gel chromatography operations with respectively $CH_2Cl_2$/AcOEt (94:6) and $CH_2Cl_2$/AcOEt (96:4) mixtures as eluants. The fraction containing the pure product after the second column is evaporated to dryness leading to 0.78 g of a solid which is recrystallised twice in hot air in EtOH, leading to 0.24 g of the title product (10% yield).

In addition to the characteristics listed in Table 1, the nuclear magnetic resonance spectrum and the mass spectrum were also effected which confirm the structure and purity of the expected compound: $^1$H-RMN (200 MHz, $CDCl_3$): 1.41–1.61 (m, 8H, aliph.); 1.65–1.93 (m, 8H, aliph.); 2.54 (s, 12H, $CH_3$); 4.03 (t, 4H, $OCH_2$); 4.10–4.22 (m, 4H, $CO_2CH_2$; 4H, $CO_2CHC\underline{H}_2$); 4.74 (d, 1H, $CO_2CHC\underline{H}$); 5.12 (t, 1H, $CO_2CHC\underline{H}$); 5.48 (ddd, 1H, $CO_2CH$); 5.54 (m, 1H, $CO_2CH$); 5.83 (dd, 2H, vinyl.); 6.13 (dd, 2H, vinyl.); 6.42 (dd, 2H, vinyl.); 6.68 (s, 4H, arom.); 7.86 (d, 4H, arom.); 8.16 (d, 2H, arom.); 8.23 (d, 2H, arom.). MS: 959 $(M)^+$.

EXAMPLE 3

2-[4'-(6-Acryloyloxyhexyloxy)-2'.5'-methylazophenyl-4-carbonyloy]—5-[4-(6-Acryloyloxyhexyloxy)benzoyl]-1.4:3.6-D-glucitol (209sf)

As can be seen in the formula developed in Table 1, this compound has only one photo-isomerisable group. In order to obtain it the operating conditions of the fifth step of example 3 are modified, in particular by using a high excess of dianhydro-D-glucitol and a shorter reaction time, so as to obtain first of all a mono-ester. The different reactivity of the endo and exo forms, and their different behaviour during silicon gel chromatography allow one to obtain selectively the exo form which will be used in the present example or the endo form which will be used, in the two following examples.

1st Step: Obtaining 209s-Mono-ester-exo and 209s-Mono-ester-endo Intermediates 4.15 g (9.78 mmol) of 200s are dissolved in 200 ml of DME and cooled to −30° C. 1.12 g (10.56 mmol) of $CH_3SO_2Cl$ then 2.12 g (20.95 mmol) of TEA are added and the mixture is maintained for 1 h30 at −300° C. A solution of 9.5 g (65.00 mmol) of dianhydro-D-glucitol in 50 ml of DME then 1.30 g (10.64 mmol) of 4-DMAP are added. Cooling is stopped and the reactional mixture is stirred overnight at ambient temperature before being hydrolysed with diluted aqueous HCl and decanted into a separating funnel. The aqueous phase is extracted with $CH_3Cl_3$ until it becomes colourless. The organic phases are regrouped, dried over $MgSO_4$ and the solvent removed in a rotating evaporator leading to 6.0 g of a solid which is purified by silicon gel chromatography.

A first fraction with $CH_2Cl_2$/AcOEt (95:5) as eluant is collected containing inter alia the diesterification product 209s. A second fraction with $CH_2Cl_2$/AcOEt (85:15) as eluant is collected, evaporated to dryness and the solid thereby obtained is hot recrystallised in hexane, leading to 1.30 g of 209s-mono-ester-exo (24% yield).

The nuclear magnetic resonance spectrum of this compound is as follows:

$^1$H-RMN (200 MHz, $CDCl_3$): 1.41–1.62 (m, 4H, aliph.); 1.68–1.93 (m, 4H, aliph.); 2.53 (s, 6H, $CH_3$); 3.64 (dd, 1H, $CH(OH)C\underline{H}_2$); 3.96 (dd, 1H, $CH(OH)C\underline{H}_2$); 4.02 (t, 2H, $OC\underline{H}_2CH_2$); 4.10–4.22 (m, 2H, $CO_2CH_2$; 2H, $CO_2CHC\underline{H}_2$); 4.37 (ddd, 1H. $C\underline{H}OH$); 4.67 (d, 1H, $CO_2CHC\underline{H}$); 4.75 (t, 1H, $CH(OH)C\underline{H}$); 5.51 (d, 1H, $CO_2CH$); 5.82 (dd, 1H, vinyl.); 6.12 (dd, 1H, vinyl.); 6.41 (dd, 1H, vinyl.); 6.67 (s, 2H, arom.); 7.86 (d, 2H, arom.); 8.15 (d, 2H, arom.).

A third fraction with $CH_2Cl_2$/AcOEt (75:25) as eluant is collected, evaporated to dryness and the solid thereby obtained is hot recrystallised in hexane to lead to 2.59 g of 209s-mono-ester-endo (48% yield).

The nuclear magnetic resonance spectrum of this compound is as follows:

$^1$H-RMN (200 MHz, $CDCl_3$): 1.42–1.61 (m, 4H, aliph.); 1.66–1.86 (m, 4H, aliph.); 2.54 (s, 6H, $CH_3$); 3.93–4.05 (m, 2H, $OC\underline{H}_2CH_2$; 2H, $CO_2CHC\underline{H}_2$; 2H, $CH(OH)C\underline{H}_2$); 4.19 (t, 2H, $CO_2CH_2$); 4.39 (m, 1H, $C\underline{H}OH$); 4.47 (d, 1H, $CH(OH)C\underline{H}$); 5.02 (t, 1H, $CO_2CHC\underline{H}$); 5.43 (ddd, 1H, $CO_2CH$); 5.82 (dd, 1H, vinyl.); 6.13 (dd, 1H, vinyl.); 6.41 (dd, 1H, vinyl.); 6.67 (s, 2H, arom.); 7.87 (d, 2H, arom.); 8.19 (d, 2H, arom.).

2nd Step: Obtaining the Title Compound 3.67 g (12.55 mmol) of 4-(6-acryloyloxhexyloxy)benzoic acid are dissolved in 150 ml of DME and cooled to −25° C. 1.42 g (12.40 mmol) of $CH_3SO_2Cl$ then 2.54 g (25.10 mmol) of TEA are added and the mixture is maintained one hour at −25° C. 3.34 g (6.04 mmol) of 209s-mono-ester-exo prepared in the preceding step dissolved in 30 ml of DME then 0.76 g (6.22 mmol) of 4-DMAP are added. Cooling is stopped and the reactional mixture is stirred one more night at ambient temperature before being refluxed with heating for six hours. After cooling, the reactional mixture is hydrolysed with diluted aqueous HCl and decanted into a separating funnel. The aqueous phase is extracted with $CH_2Cl_2$ until the aqueous phase is colourless. The organic phases are grouped, dried on $MgSO_4$ and the solvent removed in a rotating evaporator, giving residue which is purified by silicon chromatography with a $CH_2Cl_2$/AcOEt (96:4) eluant. The fraction containing the pure product is evaporated to dryness and the solid hot recrystallised in EtOH, leading to 3.65 g of the title product (73% yield).

In addition to the characteristics noted in Table 1, the nuclear magnetic resonance spectrum and the mass spectrum were effected, which confirm the purity and structure of the expected product:

$^1$H-RMN (200 MHz, $CDCl_3$): 1.42–1.60 (m, 8H, aliph.); 1.67–1.95 (m, 8H, aliph.); 2.54 (s, 6H, $CH_3$); 4.00–4.22 (m, 4H, CO$_2$CH$_2$; 4H, OCH$_2$CH$_2$; 4H, CO$_2$CHCH$_2$); 4.72 (d, 1H, CO$_2$CHCH); 5.09 (t, 1H, CO$_2$CHCH); 5.43 (ddd, 1H, CO$_2$CH); 5.52 (m, 1H, CO$_2$CH); 5.83 (dd, 2H, vinyl.); 6.13 (m, 2H, vinyl.); 6.42 (m, 2H, vinyl.); 6.68 (s, 2H, arom.); 6.93 (d, 2H, arom.); 7.86 (d, 2H, arom.); 8.04 (d, 2H, arom.); 8.15 (d, 2H, arom.). MS: 827 (M+H)$^+$.

EXAMPLE 4

2-[4-(6-Acryloyloxyhexyloxy)benzoyl]-5-[4'-(6-acryloyloxyhexyloxy)-2',5'-methylazophenyl-4-carbonyloyl]-1,4;3,6-D-glucitol (209fs)

4.40 g (15.05 mmol) of 4-(6-acryloyloxyhexyloxy) benzoic acid are dissolved in 200 ml of DME and cooled to −25° C. 1.70 g (14.84 mmol) of CH$_3$SO$_2$Cl then 3.04 g (30.04 MMOL) of TEA are added and the mixture is maintained one hour at −25° C. 4.01 g (7.26 mmol) of 209s-monoester-endo dissolved in 30 ml of DME then 0.88 g (7.20 mmol) of 4-DMAP are added. Cooling is stopped and the reactional mixture is stirred for one more night at ambient temperature before being refluxed with heating for six hours. After cooling, the mixture is hydrolysed with diluted aqueous HCl and decanted into a separating funnel. The aqueous phase is extracted with CH$_2$Cl$_2$ until the aqueous phase is colourless. The organic phases are grouped, dried on MgSO$_4$ and the solvent removed in a rotating evaporator, leading to a residue which is purified by silicon chromatography with a CH$_2$Cl$_2$/AcOEt (96:4) eluant. The fraction containing the pure product is evaporated to dryness and the solid hot recrystallised in EtOH, giving 4.21 g of the title product (70% yield).

In addition to the characteristics noted in Table 1, the nuclear magnetic resonance spectrum was effected, which confirms the purity and structure of the expected product:

$^1$H-RMN (200 MHz, CDCl$_3$): 1.42–1.62 (m, 8H, aliph.); 1.67–1.95 (m, 8H, aliph.); 2.54 (s, 6H, CH$_3$); 3.98–4.22 (m, 4H, C$_2$CH$_2$; 4H, OCH$_2$CH$_2$; 4H, CO$_2$CHCH$_2$); 4.69 (d, 1H, CO$_2$CHCH); 5.08 (t, 1H, CO$_2$CHCH); 5.42–5.50 (m, 2H, CO$_2$CH); 5.82 (dd, 2H, vinyl.); 6.12 (m, 2H, vinyl.); 6.41 (m, 2H, vinyl.); 6.68 (s, 2H, arom.); 6.90 (d, 2H, arom.); 7.88 (d, 2H, arom.); 7.96 (d, 2H, arom.); 8.21 (d, 2H, arom.).

EXAMPLE 5

2-[4'-(6-Acryloyloyloxyhexyloxy)-2'.5'-methylazophenyl-4-carbonloyl]-5-acrylyloyl-1.4;3.6-D-glucitol (209sa)

Like the compounds of examples 3 or 4, this compound includes only one photoisomerisable group, but it differs therefrom in that the non-photoisomerisable (but polymerisable) chain is shorter. It is obtained via the action of acrylic acid on mono-ester-endo (209s-mono-ester-endo) of dianhydro-D-glucitol, as explained hereinafter.

1.95 g (3.53 mmol) of 209s-mono-ester-endo are dissolved in 40 ml of THF. 2.40 g (19.8 mmol) of N,N-dimethylaniline then 1.00 g (11.0 mmol) of acryloyle chloride are added at ambient temperature. The mixture is stirred at ambient temperature for 5 days. The reactional mixture is concentrated to 5–10 ml taking care not to overheat it, then chromatography is rapidly effected with CH$_2$Cl$_2$/AcOEt (95:5) as eluant with the aim of removing the excess acryloyle chloride and thus reducing the risk of polymerisation. A fraction is collected and washed with NaOH 1N then HCl 1N. After drying on MgSO$_4$, the solvent is removed in a rotating evaporator leading to, a residue which is immediately purified by silicon chromatography. A first fraction with CH$_2$Cl$_2$ as eluant is collected containing impurities. The fraction with the desired product is eluted with CH$_2$Cl$_2$/AcOEt (95:5) as eluant. After removing the solvent, an oil is obtained which is crystallised after hot dissolution in EtOH. giving 1.0 g of the title product (47% yield).

In addition to the characteristics noted in Table 1, the nuclear magnetic resonance spectrum was effected, which confirms the purity and structure of the expected product:

$^1$H-RMN (200 MHz, CDC$_3$): 1.42–1.92 (m, 8H, aliph.); 2.55 (s, 6H, CH$_3$); 4.00–4.22 (m, 2H, CO$_2$CH$_2$; 2H, OCH$_2$CH$_2$; 4H, CO$_2$CHCH$_2$); 4.61 (d, 1H, CO$_2$CHCH); 5.04 (t, 1H, C$_2$CHCH); 5.34 (m, 1H, CO$_2$CH); 5.45 (ddd, 1H, CO$_2$CH); 5.83 (dd, 2H, vinyl.); 6.13 (m, 2H, vinyl.); 6.42 (m, 2H, vinyl.) 6.68 (s, 2H, arom.); 7.88 (d, 2H, arom.); 8.20 (d, 2H, arom.).

EXAMPLE 6

2-[4'-(6-Acryloyloxyhexyloxy)-2',5'-methylazophenyl-4-carbonyloy]-5-[4-(6-acryloyloxyhexyloxy) Benzoyl]-1,4;3,6-D-mannitol (210 fs)

This compound, which is a diastereoisomer of the compound described in example 3, is prepared from 1,4;3.6-dianhydro-D-mannitol with a few modifications to the experimental process. The synthesis diagram is not reproduced in FIG. 1.

1st Step: Preparation of the Monosubstituted 1.4;3.6-Dianhydro-D-mannitol Intermediate (110f-Mono-ester)

2.00 g (6.84 mmol) 4-(6-acryloyloxyhexyloxy) benzoic acid are dissolved in 150 ml of DME and cooled to −25° C. 0.80 g (6.84 mmol) of CH$_3$SO$_2$Cl then 1.40 g (13.83 mmol) of TEA are added and the mixture is maintained one hour at −25° C. A solution of 3.00 g (20.53 mmol) of 1,4;3,6-dianhydro-D-mannitol in 50 ml of DME then 2.50 g (20.46 mmol) of 4-DMAP. Cooling is stopped and the reactional mixture is stirred for one more day at ambient temperature before being hydrolysed with diluted aqueous HCl and decanted into a separating funnel. 300 ml of CH$_2$Cl$_2$ are added and the organic phase is separated, dried on MgSO$_4$ then the solvent is removed in a rotating evaporator, causing polymerisation of a part of the product. The remaining part is rapidly dissolved in CH$_2$Cl$_2$ then purified by silicon chromatography with a CH$_2$Cl$_2$/AcOEt (75:25) eluant. The fraction containing the pure product is evaporated to dryness and the solid hot recrystallised in EtOH, again causing polymerisation of part of the product. The polymer is removed by filtering and the solution is left to crystallise at ambient temperature then in the refrigerator, finally leading to 0.84 g of the product having the reference 110f-mono-ester (29% yield).

2nd Step: Obtaining the Title Compound 420 mg (0.99 mmol) of the compound prepared in the fourth step of example 1 (200s) are dissolved in 100 ml of DME and cooled to −25° C. 113 mg (0.99 mmol) of CH$_3$SO$_2$Cl then 200 mg (1.98 mmol) of TEA are added and the mixture is maintained one hour at −25° C. 800 mg (1.90 mmol) of the 11 Of-mono-ester intermediate prepared in the first step and 121 mg (0.99 mmol) of 4-DMAP are added. Cooling is stopped and the reactional mixture is agitated for one more day at ambient temperature before being hydrolysed with diluted aqueous HCl and decanted into a separating funnel. 400 ml of ether are added then the organic phase is separated, dried on MgSO$_4$ and the solvent is removed in a rotating evaporator. The residue obtained is purified a first time by silicon gel chromatography with a CH$_2$Cl$_2$/AcOEt (90:10) eluant, then a second time with a CH$_2$Cl$_2$/AcOEt (95:5) eluant. The fraction containing the pure product is evaporated to dryness leading to 109 mg of the title product (13% yield).

In addition to the characteristics noted in Table 1, the nuclear magnetic resonance spectrum and mass spectrum were effected, which confirm the purity and structure of the expected product:

$^1$H-RMN (200 MHz, CDCl$_3$): 1.41–1.61 (m, 8H, aliph.); 1.65–1.93 (m, 8H, aliph.); 2.54 (s, 6H, CH$_3$); 4.02 (t, 4H, OC H$_2$CH$_2$); 4.10–4.27 (m, 4H, CO$_2$CH$_2$; 4H, CO$_2$CHCH$_2$); 4.87–4.95 (m, 2H, CO$_2$CHC H); 5.29–5.43 (m, 2H, CO$_2$CH); 5.83 (dd, 2H, vinyl.); 6.13 (dd, 2H, vinyl.); 6.42 (dd, 2H, vinyl.); 6.68 (s, 2H, arom.); 6.92 (d, 2H, arom.); 7.88 (d, 2H, arom.); 8.05 (d, 2H, arom.); 8.23 (d, 2H, arom.). MS:827 (M+H)$^+$.

The experiments conducted, reported in examples 7 and 8 hereinafter, show that the chiral doping agents according to the invention allow the optical properties of a medium to be modified, and in particular, they allow a variable spiral pitch to be induced in a nematic liquid crystal medium as a function of the nature and duration of radiation whose wavelength may vary from visible (VIS) to ultraviolet (UV). In a preferred application, the properties of the chiral doping agents according to the invention are implemented to make a trichromatic display.

EXAMPLE 7

Specific Rotation, Solubility and HTP

For the above indicated application, the compounds must have high solubility and HTP in a nematic. These values, for a certain number of compounds according to the invention are recorded in Table 2 hereinafter. In this Table, the value of the specific rotation $[a]_\lambda^{20}$ before and after isomerisation, has been recorded for the methylene chloride concentrations indicated, and for the wavelengths mentioned.

TABLE 2

| Compound | Concentration g/100 ml CH$_2$Cl$_2$ | $[\alpha]^{20}\lambda$ before iso. | $[\alpha]^{20}\lambda$ after iso. | Solubility s (% mass) | HTP ($\mu$m$^{-1}$) |
|---|---|---|---|---|---|
| 201c | 0.06 | $-64°_{546}$ | $-135°_{546}$ | 1.5% < s < 3.0% | 20 |
| 201e | 0.1 | $-60°_{546}$ | $-114°_{546}$ | 1.5% < s < 3.0% | 19 |
| 206c | 0.09 | $-222°_{546}$ | $-81°_{546}$ | 0.6% < s < 0.8% | 13 |
| 206e | 0.09 | $-177°_{546}$ | $-19°_{546}$ | 3.0% < s < 4.0% | 11 |
| 209s | 0.05 | $-248°_{578}$ | $-129°_{578}$ | 3.0% < s < 3.9% | 35 |
| 209sf | 0.06 | $-85°_{578}$ | $-47°_{578}$ | 4.0% < s | 35 |
| 210fs | 0.06 | $+221°_{578}$ | $+198°_{578}$ | 1.9% < s < 6.0% | 17 |

With the exception of compound 210fs, it will be observed that the other compounds show a remarkable modification in their optical rotation, mostly greater than 50% which shows their aptitude to isomerisation by radiation. This Table further confirms what was already known, namely the absence of any evident correlation between the specific rotation variation and the HTP value of the compounds. This Table shows that, for the majority of the compounds studied, solubility is of the order of 3% in weight or greater and that HTP varies between 11 $\mu$m$^{-1}$ and 35 $\mu$m$^{-1}$.

EXAMPLE 8

Photomodulation of the Colour of Display Cells

By way of example, for the experiences recorded hereinafter, chiral compound 209s was used, which has a quite high HTP of 35 $\mu$m$^{-1}$ and good solubility allowing it to be incorporated in a concentration of 3.3% in a basic cholesteric material, including in particular a nematic mixture formed of biphenyls (for example available from Merck under the reference E48). The compound thus prepared is introduced into a test cell including a front substrate and a back substrate, these substrates being formed by glass plates, of 2.2×2.8 mm and 0.3 mm thick held by a sealing frame at a spacing of 6 $\mu$m. The cell includes an non brushed planar alignment layer, and a 1 cm square shape pixel including on each of the substrates an indium tin oxide (ITO) coating forming the electrodes which will allow the cell to switch from one state to another by applying an electric field. Once filled, the cell is exposed to UV radiation and the evolution of the UV-VIS spectrum is followed as a function of exposure time.

Figure 3:
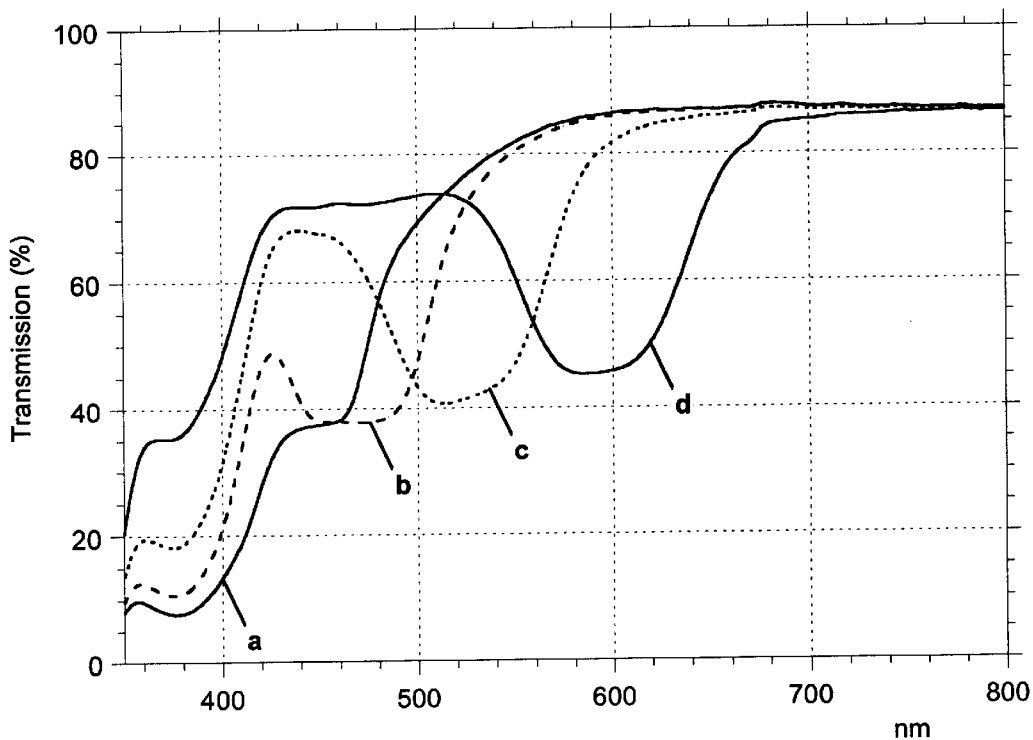
FIGS. 3 and 4 are graphs giving the transmission percentage as a function of wavelength for two cholesteric liquid crystal compositions containing a chiral doping agent according to the invention.

In the experiment corresponding to the graph of FIG. 3, giving the transmission percentage as a function of wavelength, only chiral doping agent 209s has been added to the basic cholesteric material and the initial state (curve a) and the spectrum respectively after 1 minute (curve b), 3 minutes (curve c) and 10 minutes exposure (curve d) are shown. A longer exposure time no longer modifies the spectrum, curve d representing the cell spectrum photomodulated to the maximum. A displacement will then be observed reaching 160 nm from the initial spectrum, i.e. a displacement from violet blue (curve b) to orange-red (curve d), passing through green (curve c).

Figure 4:
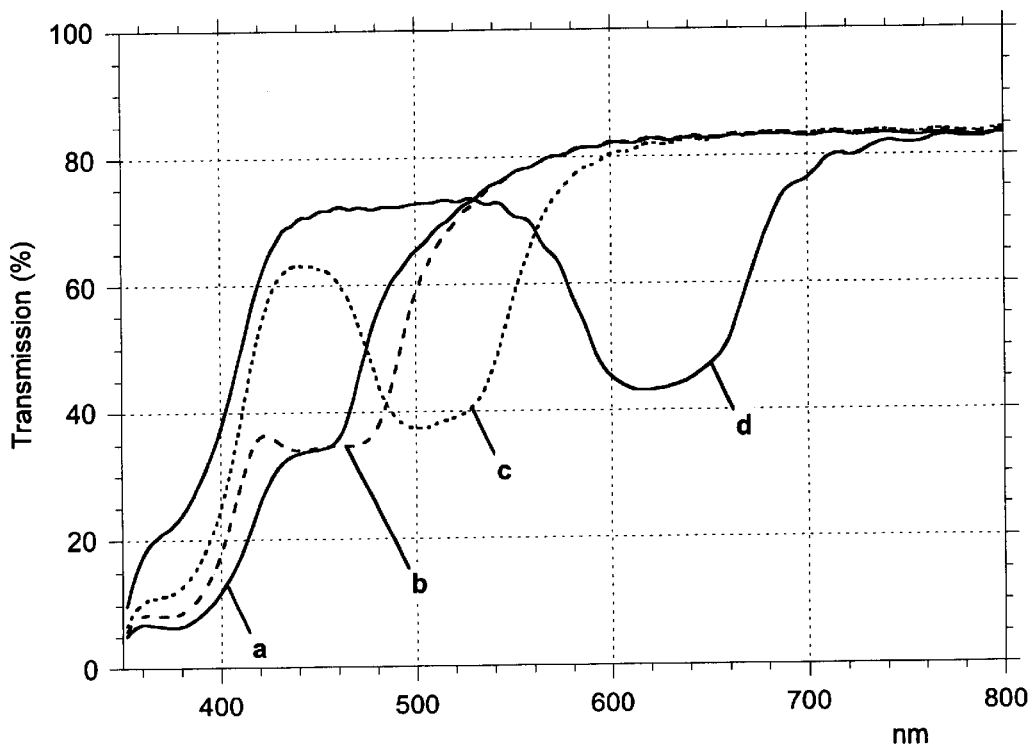

In the experiment corresponding to the graph of FIG. 4, 3% in weight of a photoinitiator of the morpholinocetone type, commercially available from Ciba-Geigy under the reference Irgacure®369, has been added to the basic cholesteric material. This photoinitiator aims to improve polymerisation of the end chains. For the purpose of improving polymerisation and thus the fixing of a determined colour, the photoinitiator may also be replaced by a discrylate type comonomer, such as the compound RM-82 available from Merck. It is also possible to use simultaneously, in appropriate ratios, both a photoinitiator and a comonomer. With reference now to FIG. 4, which concerns a cell whose basic cholesteric material only contains one doping agent according to the invention and a photoinitiator. Four curves representing respectively the initial state (curve a), the spectrum after 2 minutes (curve b), 5 minutes (curve c) and 18 minutes (curve d) are shown. A variation of 190 nm can be observed between the initial spectrum and the spectrum of the cell photomodulated to the maximum.

By replacing chiral doping agent 209s with chiral doping agent 209sf at a concentration of 4.1% in weight, in the above experiment, a variation of 220 nm would be observed after 5 minutes in the same conditions.

EXAMPLE 9

First Embodiment of a Trichromatic Cell

Compound 209sf (example 4) which showed a very good aptitude for modifying the spiral pitch of the cholesteric material with a window of 220 nm was used for the preparation of multi-coloured display cells. From identical cells to those used in example 8 with no partitions and containing only one monochrome material a cell with three zones of different colour (blue, green and red) was made by selectively or progressively masking three zones allowing their respective radiation rate to be modulated.

Such trichromatic cells may either display information, or be used as a coloured filter in a display assembly.

In a so-called "dissociative" process, each family of pixels is individually photomodulated, the two other families of pixels being covered by a mask forming a barrier to the rays, the process being repeated for each of the three families varying the radiation time of each family.

Of course, since a display cell includes a very large number of pixels of very small dimensions, the masking operations are effected by means of masks formed or obtained by known methods such as photolithographic techniques.

Figure 5:
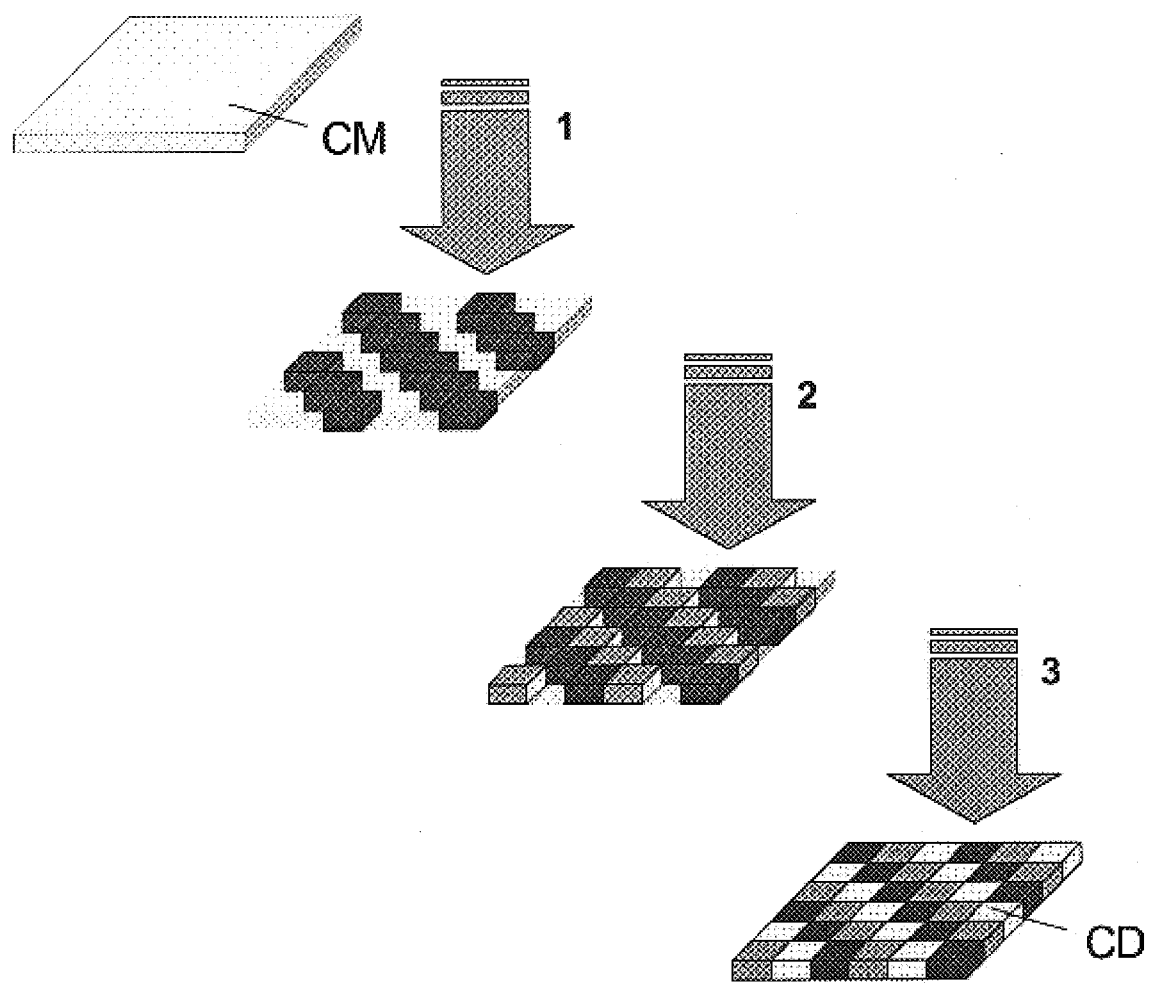
FIG. 5 shows schematically an embodiment of a trichromatic cell.

This process is schematically shown in FIG. 5. It can be seen that, starting from a chemical composition of an identical cholesteric material CM for all the pixels, in a first step 1 a family of blue pixels (B), then in a second step 2 a family of green pixels (G), and in a third step 3 a family of red pixels (R) are created to form a trichromatic display CD.

Figure 6:
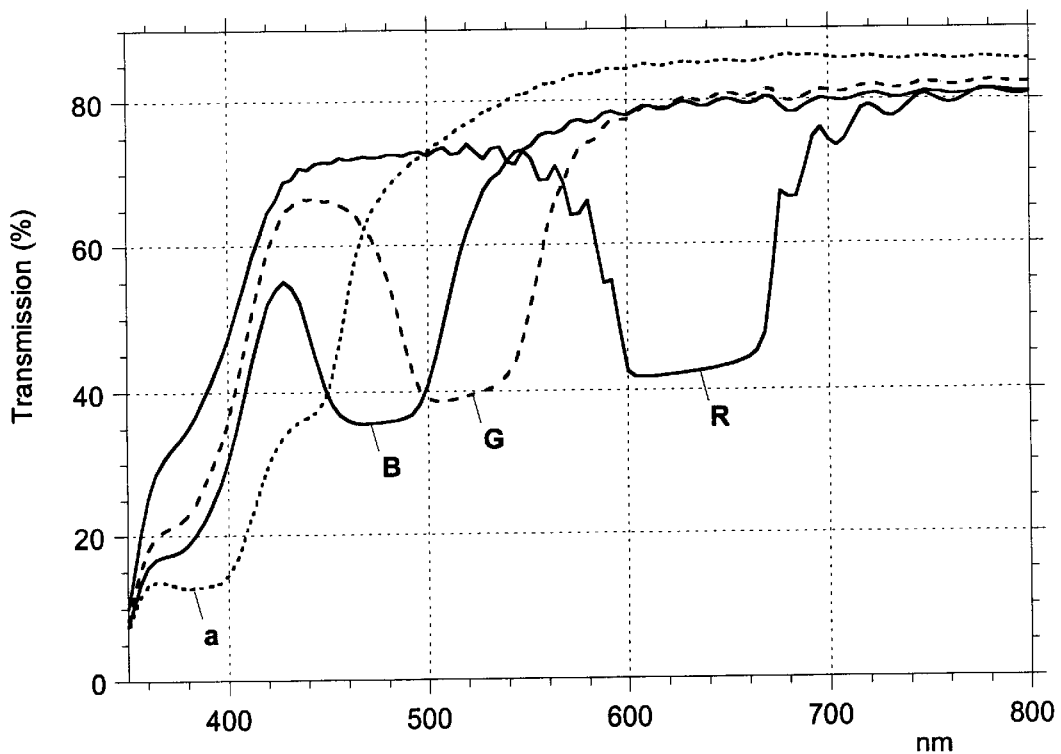
FIGS. 6 and 7 are graphs giving the transmission percentage as a function of wavelength for two embodiments of a trichromatic cell.

The graph of FIG. 6 gives the transmission percentage as a function of wavelength, at the initial state (curve a), for the blue-coloured pixels (curve B), for the green-coloured pixels (curve G) and for the red-coloured pixels (curve R).

EXAMPLE 10

Second Embodiment of a Trichromatic Cell

In this second embodiment pixelisation is achieved in accordance with a so-called "additive" process. The entire cell, i.e. all the pixels having to define the three colours, is subjected to a first period of exposure, then a family of pixels is masked and the exposure is continued for a second period and finally a second family of pixels different from the preceding one is in turn masked and exposure is finished during a third period.

Figure 7:
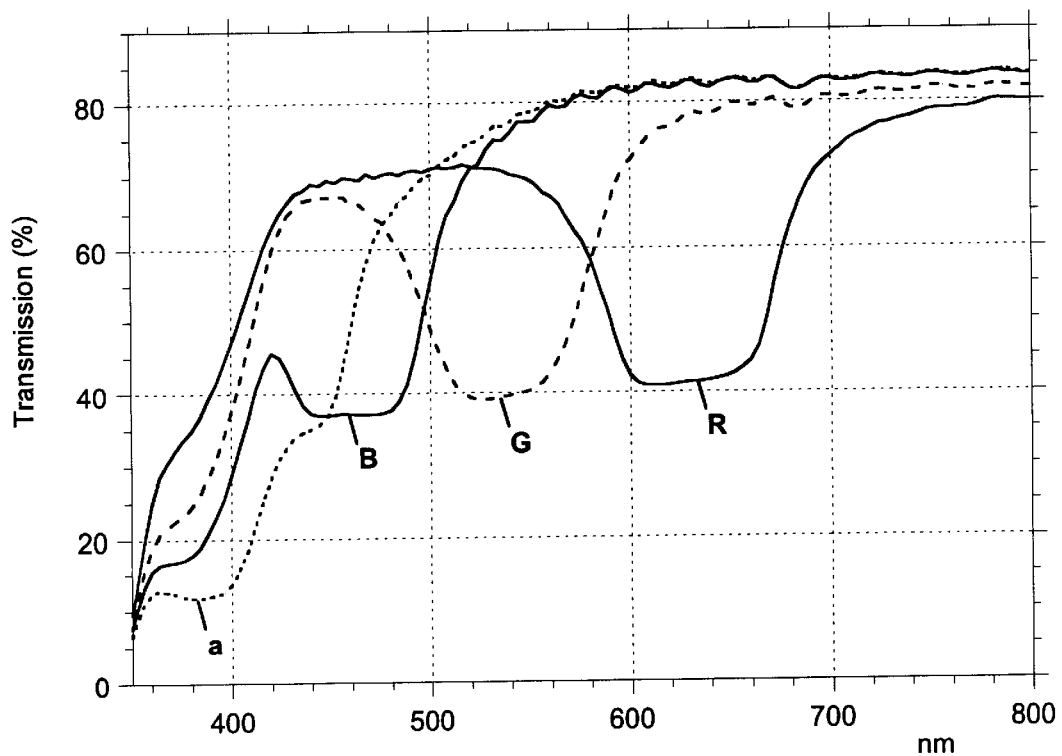

With a cell having the same features as those of example 9, and for identical exposure periods for each pixel family, the graph giving the transmission percentage as a function of wavelength shown in FIG. 7 is obtained.

Comparing the graphs of FIGS. 6 and 7, it will be observed that there are no significant differences between the "dissociative" process and the "additive" process.

EXAMPLE 11

Third Embodiment of a Trichromatic Cell

In the embodiments of examples 9 and 10 hereinbefore, it was indicated that there was no partitioning between the bottom substrate and the top substrate to delimit the individual pixels. These embodiments are satisfactory when strong polymerisation of the medium can be obtained. In the opposite case, and according to a third embodiment, it is possible to provide a "honeycomb" or channel structuration of the bottom substrate which, after filling with a single composition of a cholesteric material according to the invention, allows the pixels to be physically isolated from each other. Of course, photomodulation of each pixel family may be obtained in accordance with a "dissociative" process or an "additive" process, as indicated previously.

EXAMPLE 12

Fourth Embodiment of a Trichromatic Cell

In the embodiments of examples 9 to 11, the use of pixels allows a colour display to be obtained, i.e. the perception by the observer of an image coloured by combining the pixels of a same image point. The fourth embodiment in a way constitutes a simplification in that the display surface is divided into several photomodulable zones each having a sub-family of pixels allowing information to be displayed in a single determined colour, and thus to distinguish very simply different categories of information. This embodiment in no way excludes providing a zone made in accordance with one of the other three embodiments.

What is claimed is:

1. Chiral doping agents allowing modification in the spiral pitch of a cholesteric liquid crystal composition to be induced, wherein the chemical structure of said doping agents includes a biactivated chiral unit, at least one of whose functions allows a chemical link to be established with an isomerisable group, said group possibly having a polymerisable or co-polymerisable end chain.

2. The chiral doping agents according to claim 1, having the following formula 1:

$$A_1-Y_1-X-Y_2-A_2 \qquad (I)$$

wherein x represents a chiral radical derived from a biactivated compound, $Y_1$ and $Y_2$ are identical or different and each represent a functional linking unit selected from among —O—, —S—, —COO—, —OCO—, —CON(R)— and —N(R)CO—where R represents an alkyl residue, $A_1$ represents a photoisomerisable mesogenic group corresponding to the formula (II):

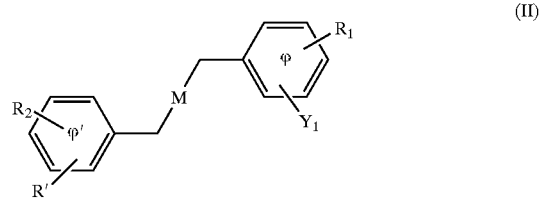

(II)

wherein two phenyl residues φ and φ' are linked by a photoisomerisable —M—bivalent radical selected from among —N=N—, —N=CH—, —CH=N— and —CH=CH—; said phenyl residues having respectively one or more substituents $R_1$, $R_2$ which are different or identical selected from among hydrogen, the alkyl or alkoxy radicals from $C_1$ to $C_5$, the halogens, and the cyano, nitro or trifluoromethyl radicals; and R' represents hydrogen or a group corresponding to the formula (III):

$$-Y_3-C_nH_{2n}-Z \qquad (III)$$

wherein $Y_3$ has the same significance as $Y_1$ and $Y_2$ or represents phenylene, n is an integer number comprised between 0 and 12 and Z represents hydrogen or a polymerisable moiety selected from among the acryloyl and acryloyloxy moieties; and A2 has the same significance as the groups of formula (II) or formula (III).

3. The chiral doping agents according to claim 2, wherein the —M—bivalent radical is the radical azo-N=N— to form with the moieties φ and φ' an azophenyl radical and in that the substituents R and $Y_1$ or $Y_2$ occupy the same ortho, meta or para positions respectively on moieties φ and φ'.

4. The chiral doping agents according to claim 2, wherein $A_1$ and $A_2$ each correspond to a photoisomerisable mesogenic group of formula II.

5. The chiral doping agents according to claim 2, wherein $A_2$ corresponds to the group of formula III.

6. The chiral doping agents according to claim 2, wherein R represents a group of formula III and in that Z still represents a polymerisable radical selected from among the acryloyl and acryloyloxy radicals.

7. The chiral doping agents according to claim 2, wherein the chiral radical agent X is derived from a diacidi or a chiral diol.

8. The chiral doping agents according to claim 2, wherein the chiral radical X corresponds to the biactivated radicals derived from dianhydro-glucitol or dianhydro-mannitol.

9. The chiral doping agents according to claim 8, corresponding to the following compound:

2,5-Bis[4'-(6-acryloyloxyhexyloxy)-2',5'-méthylazophényl-4-carbonyloyl]-1,4;3,6-dianhydro-D-glucitol.

10. The chiral doping agents according to claim 8, corresponding to the following formula:

2-[4'-(6-acryloyloxyhexyloxy)-2',5'-méthylazophényl-4-carbonyloyl]-5-[4-(6-acryloyloxyhexyloxy)benzoyl]-1,4;3,6-D-glucitol.

11. The Method for modulating chiral doping agents according to claim 1, wherein the modification to the spiral pitch induction of said chiral doping agents is obtained by ultraviolet (UV), visible (VIS) or mixed (UV+VIS) radiation acting on the isomerisable group, the radiation time being controlled to define determined colour when said doping agents are incorporated in a cholesteric liquid crystal composition.

12. A display cell including two transparent substrates, supporting electrodes connected to an electronic circuit, and a sealing frame delimiting together a lamellar space into which a cholesteric liquid crystal composition is introduced incorporating at least a chiral doping agent according to claim 1, wherein the cell is subjected to ultraviolet (UV) or visible (VIS) radiation modulated as a function of different zones, or different pixel families by using masks and varying the radiation time.

13. The display cell according to claim 12, wherein each family of pixels corresponds to a determined mask allowing the radiation time of each family to be adjusted.

14. The display cell according to claim 12, wherein masks are designed to successively uncover each pixel family and to allow the progressive radiation thereof.

15. The display cell according to claim 12, wherein it does not include any partitioning, and in that the chiral doping agents have a polymerisable or co-polymerisable end chain.

16. The display cell according to claim 12, wherein it includes partitions for each zone or for each pixel, and in that the chiral doping agents may not include a polymerisable or co-polymerisable end chain.

* * * * *